United States Patent [19]

Yoshida

[11] 4,302,773
[45] Nov. 24, 1981

[54] DEFECT INSPECTION SYSTEM
[75] Inventor: Hajime Yoshida, Tokyo, Japan
[73] Assignee: Hajime Industries Ltd., Tokyo, Japan
[21] Appl. No.: 121,516
[22] Filed: Feb. 14, 1980
[30] Foreign Application Priority Data
   Feb. 20, 1979 [JP] Japan ................... 54-18868
[51] Int. Cl.³ ............................................. H04N 7/18
[52] U.S. Cl. .................................. 358/106; 250/562; 356/237
[58] Field of Search ............... 358/106, 107; 250/562, 250/872; 356/237
[56] References Cited
U.S. PATENT DOCUMENTS
   4,160,998  7/1979  Kamin ........................ 358/108

*Primary Examiner*—Marc E. Bookbinder
*Assistant Examiner*—Edward L. Coles

[57] ABSTRACT

A defect inspection system which inspects the defects on an object to be inspected by photosensing the inspected object with a monochrome television camera. A pair of detection circuits are provided which receive such image signal corresponding to the inspected object from the television camera and have different sensitivities so that both or only one of the pair outputs a signal in accordance with the rate of change of the image signal level with respect to time. Both of the outputs from the pair of detection circuits are supplied to a mixer circuit. In this case, the mixer circuit is so formed that it will only output a defect detection signal when only one of the above mentioned pair of detection circuits shall output a signal.

6 Claims, 15 Drawing Figures

DEFECT INSPECTION SYSTEM

BACKGROUND OF THE INVENTION

1. Field of the Invention

The present invention is generally related to a defect inspection system which inspects the defects on an object to be inspected and directed more particularly to a defect inspection system which especially utilizes a monochrome television camera for automatic defect inspection of an object to be inspected.

2. Description of the Prior Art

Systems are already proposed for the inspection of the defects on an object to be inspected by a monochrome television camera under the prior art, which generally picks up each of the inspected objects by a television camera by which the image of the object is reproduced on a monitor television receiver and then observed to check the existence of a defect or not. Accordingly, the defect inspection efficiency of the prior art was poor and an automatic operation of the inspection for defects on inspected objects was practically considered impossible.

OBJECTS AND SUMMARY OF THE INVENTION

Accordingly, it is a main object of the present invention to provide a novel defect inspection system free from the defect encountered in the prior art.

It is another object of the invention to provide a defect inspection system in which a monochrome television camera is contained to automatically carry out the defect inspection of objects.

It is a further object of the invention to provide a defect inspection system which can automatically inspect the defect of an object accurately even if the defect is fine.

According to an aspect of the invention a defect inspection system is provided which comprises:

(a) means for picking up an object to be inspected to produce a video signal thereof;

(b) a plurality of detecting means connected to said picking up means to receive the video signal therefrom, detecting sensitivities of said plurality of detecting means being so selected that all or some of said plurality of detecting means produce signals in response to the rate of level change of said video signal with respect to time; and (c) means connected to said plurality of detecting means for producing a defect detection signal when some of said plurality of detecting means produce the signal The other objects, features and advantages of the present invention will become apparent from the following description taken in conjunction with the accompanying drawings.

DESCRIPTION OF THE PREFERRED EMBODIMENT

One example of the defect inspection system under the present invention shall be explained in reference with the attached drawings hereunder.

Figure 1:
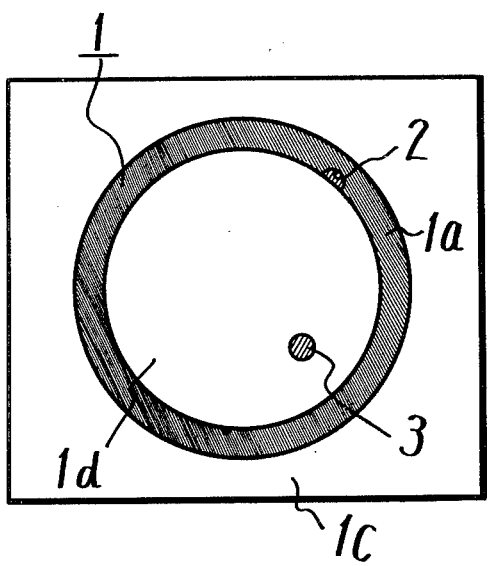
FIG. 1 shows a top plan view of an object to be inspected.
Figure 2:
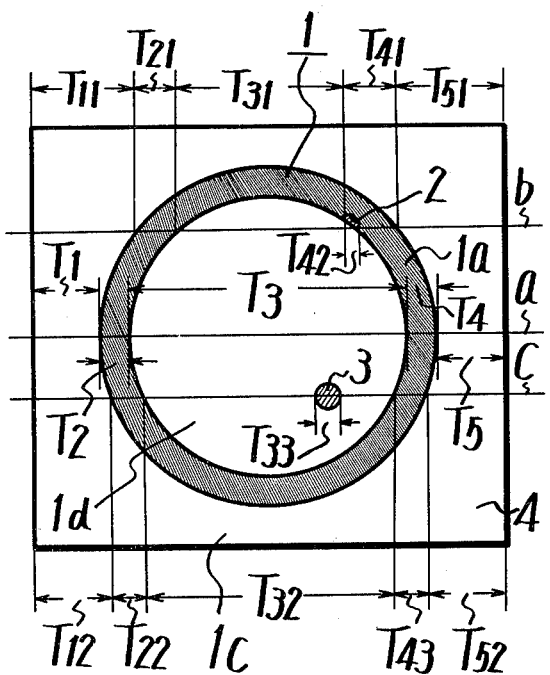
FIG. 2 shows the screen of a monitor television receiver on which the image of the object is reproduced.

FIG. 1 is the top plan view of an object to be inspected such as a bottle cap placed up side down as one example, and FIG. 2 is the top plan view of the object on a monitor television receiver on which the image of the object is reproduced with a monochrome television camera. On FIGS. 1 and 2, 1 is the inspected object such as caps, 2 is a dent or crack at the side wall portion of cap 1, in other words a defect portion, and 3 is a foreign material such as dust or the like or a defect on the bottom of the cap 1. Further, 4 on FIG. 2 is the screen of the monitor television receiver.

Figure 3:
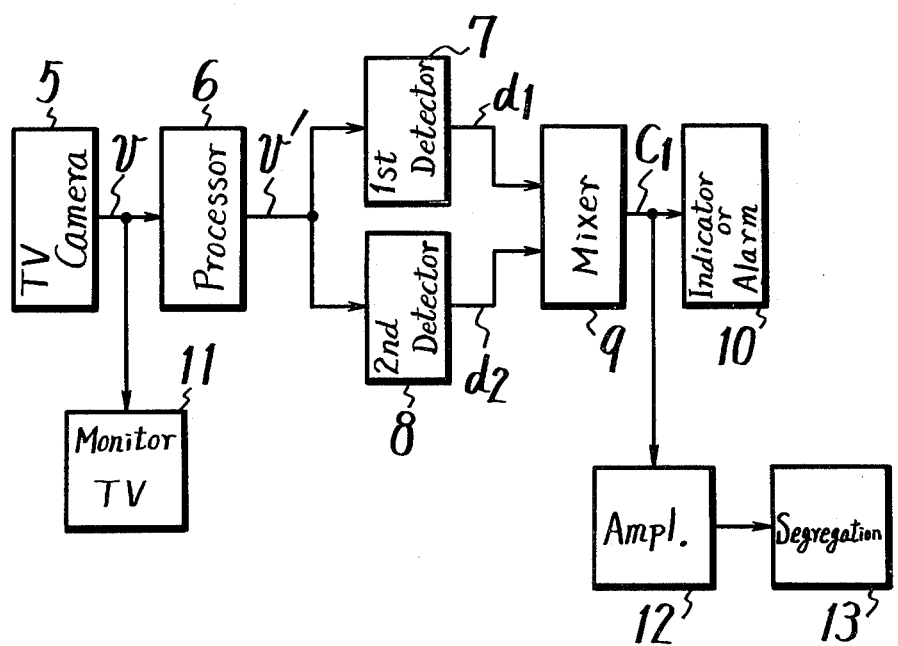
FIG. 3 is a systematic block diagram to show an example of the defect inspection system under the present invention.
Figure 4A:
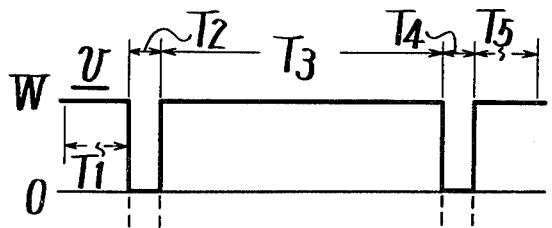
FIGS. 4, 5 and 6 are respectively, waveform diagrams used to explain the functions of the example of the invention shown on FIG. 3.
Figure 4B:
Figure 4C:
Figure 4D:

On FIG. 3, a systematic block diagram of an example of the defect inspection system under the present invention is shown, on which 5 is a monochrome television camera, by which the inspected object 1 as indicated on FIG. 1 is picked up. A video or image signal v from television camera 5 is supplied to an analog processor circuit 6 made of, for example, an amplifier and a low pass filter, at where the image signal v is amplified as necessary and also the unnecessary contents thereof are removed. An output v' from analog processor circuit 6 is supplied to 1st and 2nd detector circuits 7 and 8. The 1st and 2nd detector circuits 7 and 8, each made of, for example, a level comparator and one-shot multivibrator, have different detection sensitivities as later described, which in response to the rate of the level changes of the image signal v' as supplied with respect to time, generate output signals d1 and d2 respectively. Output signals d1 and d2 from the 1st and 2nd detector circuits 7 and 8 are supplied to a mixer circuit 9 such as an exclusive OR circuit. The mixer circuit 9 is generally an exclusive logic circuit, whereas an output is not generated when both the output signals d1 and d2 are simultaneously supplied from the 1st and 2nd detector circuits 7 and 8 but an output signal c1 is only produced when either one only of the output signals d1 or d2 is supplied. Output signal c1 from the mixer circuit 9 is supplied to an indicator or alarm section 10 so that when the output c1 is supplied thereto, for instance a lamp or a buzzer will be driven to indicate or generate an alarm.

As a next step, the function of the example of the present invention as shown on FIG. 3 will be explained in reference with the waveform diagrams as shown on FIG. 4A, 4B, 4C, 4D, FIG. 5A, 5B, 5C, 5D and FIG. 6A, 6B, 6C, 6D.

The image signal v from television camera 5 as shown on A of FIG. 4 is corresponding to one horizontal line a on FIG. 2, and at this horizontal line a there is no defect on cap 1 which in this example is the inspected object (we shall assume that the side wall portion $1a$ of cap 1 is black while the background $1c$ as well as the bottom portion $1d$ of cap 1 are white), so that the image signal v is on white level W at periods T1, T3 and T5 which correspond to the background $1c$ while it is on black level o at the periods T2 and T4 which correspond to the side wall portion $1a$ of cap 1. In this case, on the image signal v there is no other portions than the black level O or the white level W. In this case, the 1st and 2nd detector circuits 7 and 8 equally output pulse signals d1 and d2 when image signal v falls from the white level W to the black level O or at the reversed times as shown on FIGS. 4B and 4C. Since the mixer circuit 9 which is supplied with both of the output pulse signals d1 and d2 as mentioned above, is an exclusive logic circuit, when the 1st and 2nd detection circuits 7 and 8 simultaneously output the signals d1 and d2, an output is not produced from the mixer circuit 9. Therefore, the indicator or the alarm section 10 will not be driven. In other words, when the inspected portions of the inspected object 1 is complete, mixer circuit 9 will not output a signal and accordingly, the indicator or the alarm section 10 will not show any indication.

Figure 5A:
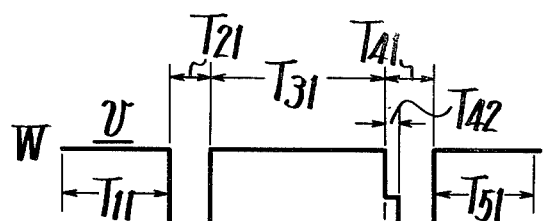
Figure 5B:
Figure 5C:
Figure 5D:

However, in the case of observing portions of the horizontal line b on FIG. 2, for the periods of T11, T21, T31 and T51, there is no defect portion in the same manner as periods T1, T2, T3 and T5 on line a, but on portions of period T41 the crack 2 exists as a defect between period T42 which is a portion of period T41 and in this case, the image signal v as shown on FIG. 5A, shows a waveform which includes a half level portion that is lower than the white level W but still higher than the black level O at period T42. The sensitivities of the 1st and 2nd detector circuits 7 and 8 which receive the image signal v' responding to the image signal v are respectively arranged as follows. That is, while the 1st detector circuit 7 shall output pulse signal d1 at all of the falls and rises of image signal v (refer to FIG. 5B), the 2nd detector circuit 8 does not output pulse signal d2 at the point of falls responding to the half level portion of the image signal v (refer to FIG. 5C). Accordingly, in this case at the time when the end detector circuit 8 does not output a pulse signal, while only the 1st detector circuit 7 outputs pulse signal d1, the mixer circuit 9 outputs a detection pulse signal c1 as shown on FIG. 5D. In other words, the time when the mixer circuitry 9 outputs pulse signal c1, is when there is a defect such as crack 2 on the side wall 1a of the inspected cap 1. In this case, the indicator section or alarm section 10 is driven by the pulse signal c1 and alarms or indicates that there is a defect existing on the inspected object 1.

Figure 6A:
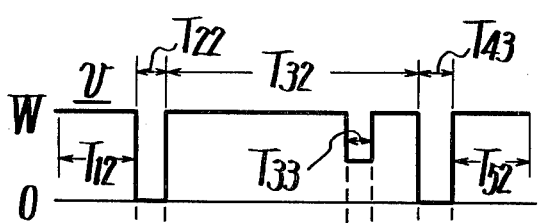
Figure 6B:
Figure 6C:
Figure 6D:

As a next step, on FIG. 2, a horizontal line c will have portions such as periods T12, T22, T43 and T52 responding to portions which like periods T1, T2, T4 and T5 of line a do not contain any defective portion, but at portions of period T33 of period T32, defects such as the foreign object 3 exist so that the image signal v at line c which is shown on FIG. 6A includes portions where the level at the portion of period T33 is lower than the white level W but higher than the black level O. Therefore, the 1st detector circuit 7 outputs pulse signal d1 as shown on FIG. 6B in corresponding to all of the level changes in the image signal v, while the 2nd detector circuit 8, as shown on FIG. 6C, does not output a pulse signal for the portions of half level changes of the image signal v and only outputs pulse signal d2 for the level changes between white and black. Accordingly, at the mixer circuit 9 as shown on FIG. 6D, at the time when the 1st detector circuit 7 only outputs a pulse signal, detection signal c1 is output. In other words, a detection pulse signal c1 is output for the period where there is a defect existing such as foreign material 3, so that by such pulse signal c1, the indicator section or the alarm section 10 is driven to indicate the existence of a defect.

As described above, by the present invention, based upon the output of the television camera, the inspection of a defect on the inspected object can be automatically conducted.

Further, on FIG. 3, the output image signal v from the television camera 5 may be supplied to a monitor television receiver 11 so that the inspected object can at the same time be observed by the human eyes. Also, the output c1 of the mixer circuit 9 can be supplied to a proper amplifier circuit 12 so that when the inspected product is a defective product, the output from the amplifier circuit 12 may be supplied to drive a segregation system 13 for the defective product.

Further, the levels of background 1c of the inspected object 1 as well as the side wall 1a and bottom 1d do not necessarily have to be limited to the above mentioned white and black, and may be any proper level. In such case, the sensitivity of 1st and 2nd detector circuits 7 and 8 will be properly tuned to a selected level so that the relations between the outputs from the two will be as described above to obtain similar effects.

The above description is given on a single preferred embodiment of the present invention, but it will be apparent that many modifications and variations could be effected by one skilled in the art without departing from the spirits or scope of the novel concepts of the invention. Therefore, the spirits or scope of the invention should be determined by the appended claims only.

I claim as my invention:

1. A defect inspection system comprising:
   (a) pick-up means for sensing an object to be inspected and to produce a video signal thereof;
   (b) a plurality of detecting means each having respective predetermined detecting sensitivities connected in parallel to said pick-up means to simultaneously receive the video signals therefrom said, detecting sensitivities of said plurality of detecting means being so selected that all or some of said plurality of detecting means produce signals in response to a the rate of level change of said video signal with respect to time; and
   (c) means connected simultaneously to outputs of each of said plurality of detecting means for producing a defect detection signal when at least some of said plurality of detecting means produce a signal.

2. A defect inspection system according to claim 1 further including means between said pick up means and said plurality of detecting means for amplifying said video signal and removing unnecessary components thereof.

3. A defect inspection system according to claim 1 further including means connected to said last-mentioned means for indicating an alarm when said last-mentioned means produces the defect detection signal.

4. A defect inspection system according to claim 1 further including means connected to said last-mentioned means to segregate an object when said last-mentioned means delivers the defect detection signal.

5. A defect inspection system as claimed in claim 1, in which said pick up means is a monochrome television camera.

6. A defect inspection system according to claim 5 further including a monitor television receiver connected to said television camera to reproduce an image of said object to be observed by a human eye.

* * * * *